United States Patent [19]

Slade et al.

[11] Patent Number: 5,200,215
[45] Date of Patent: Apr. 6, 1993

[54] ENZYME TREATED LOW MOISTURE CONTENT COMESTIBLE PRODUCTS

[75] Inventors: Louise Slade; Harry Levine, both of Morris Plains; Stuart Craig, Morristown; Henry Arciszewski, Franklin Lakes; Susan Saunders, Randolph, all of N.J.

[73] Assignee: Nabisco, Inc., Parsippany, N.J.

[21] Appl. No.: 781,646

[22] Filed: Oct. 25, 1991

Related U.S. Application Data

[63] Continuation of Ser. No. 183,927, Apr. 20, 1988, abandoned.

[51] Int. Cl.$^5$ .............................................. A21D 8/04
[52] U.S. Cl. ......................................... 426/18; 426/28
[58] Field of Search .................................... 426/18, 28

[56] References Cited

U.S. PATENT DOCUMENTS

| | | |
|---|---|---|
| 2,821,501 | 1/1958 | Simpson . |
| 3,512,992 | 5/1970 | Cooke et al. . |
| 4,435,429 | 3/1984 | Burrows et al. ...................... 426/18 |
| 4,746,517 | 5/1988 | Ducroo .................................. 426/12 |
| 4,748,032 | 5/1988 | Kono et al. ......................... 426/321 |
| 5,066,218 | 11/1991 | Silver .................................... 426/20 |

FOREIGN PATENT DOCUMENTS

| | | |
|---|---|---|
| 603953 | 8/1960 | Canada . |
| 927826 | 6/1973 | Canada . |
| 180952 | 11/1985 | European Pat. Off. . |
| 227159 | 1/1987 | European Pat. Off. . |
| 2227368 | 10/1974 | Fed. Rep. of Germany . |
| 141297 | 9/1981 | Japan . |
| 141298 | 9/1982 | Japan . |
| 1332903 | 10/1973 | United Kingdom . |
| 2150933A | 7/1985 | United Kingdom . |

OTHER PUBLICATIONS

"Separation of Starch And Gluten" by Simpson, Canadian Jnl. of Tech., vol. 33, pp. 33–44 (1955).
Kulp, K., "Enzymolysis of Pentosans of Wheat Flour," *Cereal Chemistry*, vol. 45, pp. 339–350 (1968).
Chem Abstract No. 71839j vol. 82 pp. 347–348 (1975).
Medcalf et al "Structural Characterization of a Pentosan from the Water Insoluble Portion of Durum Wheat Endosperm," *Cereal Chemistry*, vol. 45, pp. 550–556 Nov. 1968).
"Genencor Cellulase 150 L Genencor Cellulase 250P" by Genencor, Inc. 180 Kimball Way, South San Francisco, Calif. 94080.
Jankiewicz et al "The Effect of Soluble Pentosans Isolated from Rye Grain on Staling of Bread," *Food Chemistry*, vol. 25 pp. 241–249 (1987).
Gaines et al "Effects of Selected Commercial Enzymes on Cookie Spread and Dough Consistency," *Cereal Chemistry*, vol. 66, No. 2 pp. 73–78 (1989).

(List continued on next page.)

*Primary Examiner*—Joseph Golian

[57] ABSTRACT

Low moisture content comestibles having reduced water regain or increased tolerance to moisture are produced by enzymatically treating a farinaceous material with an enzyme composition comprising pentosanase or beta-glucanase, or mixtures thereof to reduce its net-work forming swellable water-soluble hemicellulose content. The hydrolysis of the water-soluble pentosans, beta-glucans or mixtures thereof is conducted so that a substantial portion of the hydrolysis product has a linear or backbone degree of polymerization of less than about 100, more suitably less than about 75, preferably less than about 50, most preferably less than 17. In addition, the hydrolysis is conducted so as to minimize the production of mono and/or di-saccharides. The low moisture content comestible products include low moisture content baked good such as cookies, crackers, and biscuits, farinaceous pet snacks, plant protein extracts, hot cereals, ready-to-eat cereals, low calorie flours and low calorie flour fractions. The enzyme compositions which are used are preferably substantially completely free of proteases and amylases so as to avoid reducing the functionality of proteins and starch, respectively. The comestible products have a moisture content of less than about 20 percent by weight. Hemicellulose hydrolyzates may also be produced for incorporation into comestibles.

13 Claims, No Drawings

OTHER PUBLICATIONS

Bushuk, W. "Distribution of Water in Dough and Bread," *Bakers Digest*, vol. 40 p. 38 (1966).

Palmer et al., "Influence of Enzyme Distribution on Endosperm Breakdown (Modification) During Malting" *ASBC Journal* vol. 43, No. 1 pp. 17-26 (1985).

Wieg, Von A. J. "Enzymatic Treatment of Waste Water From Wheat Starch Industry" Starch vol. 36, No. 4, pp. 135-1401 (1984).

Tegge et al., "Enzymatic Hydrolysis of Various Starches" *Starch/Staeske* vol. 38, No. 10, pp. 329-335 (1986); *Chemical Abstracts* No. 224503s vol. 105, p. 607 (1986).

Drews, "Amylograms With Respect to Some Quality Criteria of Rye and its Mill Products" Brot. Gelaeck vol. 23, No. 9, pp. 165-170 (1969); *Chemical Abstracts* vol. 72, p. 201, No. 65520a (1970).

Bruemmer, J. "Baking Components" *Brot Gelaeck* vol. 25, No. 11, pp. 217-220 (1971); Chemical Abstracts No. 98049q, vol. 76, p. 333 (1972).

Fretzdorf, B. "Determination of Beta-xylosidase Activity in Rye" *Z. Lebenson Unters. Forsch*, vol. 167, No. 6, pp. 414-418 (1978); Chemical Abstracts No. 90:82674t, vol. 90, p. 213.

Weipert, D. "Rheology of Rye Dough" *Getreide Mehl Brot.*, 26(10) pp. 275-280 (1972); Chemical Abstracts 78:56693f, vol. 78, p. 388 (1972).

Weipert, D. "Rheology of Rye Doughs" *Ber Getreidechem-Tag Detmold*, 1972 pp. 189-203; *Chemical Abstracts* 78:122859, col. 78, p. 349 (1973).

Botsch, A. "Possibilities for Utilization of New Enzymic Baking Additives" *Brot Gelaeck*, vol. 23, No. 10, pp. 202-203 (1969); *Chemical Abstracts* 72:120153k, vol. 72, p. 226 (1970).

Johansson et al., "Investigations on the Composition of Water Soluble Pentosans in Flour and Doughs of Wheat and the Effect of Pentosanases on the Machinability During Dough Development" *Sver Utasaedesforeen, Tidske*, vol. 8 (3-4), pp. 282-301 (1971).

"Grain Processing Opportunities with Genencor's GC123" by Genecor Inc., 180 Kimball Way, S. San Francisco, Calif. 94080.

Levine et al. "A Polymer Physico-Chemical Approach to the Study of Commercial Starch Hydrolysis Products" Carbohydrate Polymers 6(1986) 213-244.

Metcalf et al "Comparison of Chemical Composition and Properties Between Hard Red Spring and Durum Wheat Endosperm Pentosanes" *Cereal Chemisty* vol. 45, pp. 539-549 (Nov. 1968).

Simpson "Microbial Pentosanases" Can. J. Micro. vol. 1, No. 2, pp. 131-139 (Oct. 1954).

ENZYME TREATED LOW MOISTURE CONTENT COMESTIBLE PRODUCTS

This application is a continuation of prior U.S. application Ser. No. 07/183,927, filing date Apr. 20, 1988, abandoned.

FIELD OF THE INVENTION

This invention relates to the production of enzyme treated low moisture content comestible products such as cookies, crackers, biscuits, snacks, cocoa, flour, plant protein extracts, hot cereals, and ready-to-eat cereals. This invention also relates to hemicellulose hydrolyzate products.

BACKGROUND OF THE INVENTION

Enzyme compositions comprising pentosanases have been used to treat starch-containing compositions such as starch suspensions or solutions in starch production, brews, waste waters, doughs, and cereal products. Viscosity reduction of starch solutions, doughs, and cereal products, and purification of aqueous based starch-containing compositions are reported as resulting from the enzymatic treatment. Pentosanases have also been used to increase the softness of bread and other leavened products.

Regarding aqueous-based systems, Palmer et al, "Influence of Enzyme Distribution or Endosperm Breakdown (Modification) During Malting" *ASBC Journal*, vol. 43, no. 1, pp. 17-26 (1985) teaches that during the malting of barley, alpha-amylase, endo-beta-1,3:1,4-glucanase, pentosanase, and endo-beta-1,3-glucanases are developed. It is reported that steeping procedures and gibberellic acid can alter the pattern of enzyme development and the release and distribution of enzymes in the starchy endosperm.

Wieg, Von A. J., "Enzymatic Treatment of Waste Water From Wheat Starch Industry," *Starch*, vol. 36, no. 4, pp. 135-140 (1984) teaches the enzymatic treatment of waste-water from the wheat starch industry so as to reduce the biochemical oxygen demand of the waste water. The enzymes used to treat the waste water are alpha-amylase, cellulase, hemicellulase, beta-glucanase, and pentosanase.

Tegge et al, "Enzymic Hydrolysis of Various Starches" *Starch/Staerke*, vol. 38, no. 10, pp. 329-335 (1986) and its *Chemical Abstract* No. 224503r, vol. 105, p. 617 (1986) discloses the addition of pentosanase to commercial starches with amylolytic enzyme preparations. It is reported that the pentosanase did not affect viscosity and filtration of the hydrolyzates.

Drews, "Amylograms With Respect to Some Quality Criteria of Rye and its Mill Products," *Brot. Gebaeck*, vol. 23, no. 9, pp. 165-170 (1969) and its *Chemical Abstract* No. 65520a, vol. 72, page 261 (1970) discloses the addition of rye mucin to a wheat starch suspension. It is reported that the viscosity maximum depends on the soluble pentosans and that the removal of soluble material from rye flour considerably decreases its amylographic maximum.

Bruemmer, J., "Baking Components," *Brot. Gebaeck*, vol. 25, no. 11, pp. 217-220 (1971) and its *Chemical Abstract* No. 98049q, vol. 76, page 333 (1972) discloses the relative effects on the viscosity of rye flour suspensions exhibited by various enzymes such as protease, pentosanase, and alpha-amylase.

Fretzdorf, B., "Determination of Beta-xylosidase Activity in Rye," *Z. Lebenson Unters. Forsch*, vol. 167, no. 6, pp. 414-418 (1978) and its *Chemical Abstract* No. 90:82674t, vol. 90, page 213 (1979) discloses the determination of beta-xylosidase in rye extracts and commercial enzymes such as cellulase and pentosanase.

Regarding doughs and baked goods, Weipert, D., "Rheology of Rye Dough," *Getreide Mehl Brot.*, 26(10) pp. 275-280 (1972) and its Chemical Abstract No. 56693f vol. 78, page 388 (1972) discloses the treatment of rye dough for two hours at 30° C. with two pentosanases (EL-5-72 and EL-15-72). The article reports the attainment of softer doughs and increased bread volume. The pentosanases and proteases are taught as lowering dough viscosity the most compared to results obtain with three amylases, cellulase, a pectinase, and a malt flour. The pentosanase EL-5-72 is indicated as being free of amylase and protease activity.

Weipert, D., "Rheology of Rye Doughs," *Ber Getreidechem-Tag Detmold*, pp. 189-203 (1972) and its *Chemical Abstract* 122859t, vol. 78, page 349 (1973) discloses lowering of rye dough viscosity with enzymes. It is taught that the use of pentosanase and amylase gives more maltose and bread volume than does protease and amylase.

Great Britain patent specification no. 1,332,903 to Casier (Oct. 10, 1973) discloses that water-soluble pentosans from wheat and rye grains can have certain beneficial effects as regards to certain aspects of panification, promoting swelling, retention of water, or favoring the structure itself of the finished wheat or rye bread product. The Great Britain patent publication teaches that water-insoluble pentosans have remarkable effects on panification, making it possible to produce a perfectly edible and pleasant-tasting bread from pure starch. It is further indicated that the use of water-insoluble pentosans in the production of bread from flours such as the various soft wheat flours, cassava flour, potato flour, maize flour, rice flour, and any starch-bearing cultivated vegetable would be particularly favorable. In the process of the Great Britain patent publication, the water-insoluble pentosans are extracted for use as an adjuvant for panification and/or a gelling agent by removing most of the water-soluble components from a gramineous plant starting material, treating the residue with a sufficiently strong base to extract the water-insoluble pentosans from the residue without solubilizing the starches thereof, and electrodialyzing the extract at a pH above 6 and subsequently drying the latter. The treatment of the residue with the strong base is conducted at a temperature not exceeding 55° C. and at a pH of from 8 to 13.

Rotsch, A., "Possibilities for Utilization of New Enzymic Baking Additives," *Brot Gebaeck*, vol. 23, no. 10 pp. 202-203 (1969) and its *Chemical Abstract* No. 120153k, vol. 72, page 226 (1970) discloses the addition of microbial pentosanase to rye and wheat breads, waffles, and other bakery products. The addition of the pentosanase is reported to increase the volume and lightness and improve the crumb quality of rye and wheat breads. It is also taught that the pentosanase lowers the dough viscosity and facilitates the manufacture of waffles and other bakery products.

Canadian Patent No. 603,953 and corresponding U.S. Pat. No. 2,821,501 to Simpson disclose that in the extraction of starch from wheat which contains pentosan gum, the gum is degraded with a pentosanase enzyme but the starch itself is not degraded. To avoid attack on gluten by proteolytic enzymes, it is indicated as being preferred to remove the gluten from the flour before the enzyme is added to the starch slurry. The enzyme is prepared by aerobically growing an organism selected from the group consisting of *Bacillus pumilus, Bacillus subtilis, Bacillus licheniformis,* and *Bacillus polymyxa*. It is disclosed that the release of starch from the pentosans increases the recovery of starch from flour.

The use of pentosanases in bread doughs to influence loaf volume or crush is disclosed in: 1) Johansson et al, "Investigations on the Composition of Water Soluble Pentosans in Flour and Doughs of Wheat and The Effect of Pentosanases on the Machinability During Dough Development," *Sver Utsaedesfoeren, Tidske,* Vol. 8 (3-4) pp. 282-301 (1971) and its *Chemical Abstract* No. 117310r, vol. 75 page 140 (1971), and 2) German Offen. 2,227,368 to Krebs et al (Oct. 17, 1974) and its Chemical Abstract No. 71839j, vol. 82 page 347 (1975).

The Johansson et al article teaches that the use of an enzyme preparation known as Rhozyme HP-150 increases loaf volume without any appreciable deterioration of the crumb. It is further taught that kneading did not significantly affect the pentosan composition.

The German patent publication to Krebs et al discloses the addition to bread doughs of a composition comprising alpha-amylases, protease, pentosanase, and a swelling agent. The swelling agent may be corn starch, guar gum, carob bean flour, galactomannan, or pectin. It is reported that pentosanase favorably influences the crush.

Great Britain Patent Publication No. 2,150,933A and corresponding French Patent Publication No. 2,555,602 disclose that pentosans occur in cereal flour, in which they bind water, and they contribute to stiffening or staling of bread after baking. According to these patent publications, a reduction in the pentosan content of the flour reduces the liability to stiffening. The references teach the production of a pentosan-degrading enzyme and a composition containing it which has pentosanase activity, particularly at higher temperatures of around 90° C. The enzyme compositions are prepared by fermentation of *Talaromyces Emersonii*, particularly strain IMI 116815. The enzyme is added in aqueous medium to treat wheat flour to reduce the stiffening or staling of the bread. The enzyme composition is also used to reduce the viscosity of starch solutions in the production of starch.

U.S. Pat. No. 3,512,992 discloses the use of a pentosanase composition for increasing the softness of bread. The pentosan-degrading enzyme preparation may be derived from *Bacillus subtilis* or *Aspergillus niger*. Commercial enzyme preparations which may be used in the process of U.S. Pat. 3,512,992 are Rhozyme HP-150 sold by Rohm and Haas Co., Cellulase 4000 sold by Miles Laboratories, and Cellulase-APIII sold by Amano Pharmaceutical Co. Ltd. The Rhozyme HP-150 also contains as minor constituents, amylase, protease, pectinase and anthocyanase.

According to U.S. Pat. No. 3,512,992, bread and other leavened products are prepared by intimately combining with flour and other dough-forming ingredients, water and an enzyme preparation having a pentosanase activity of between 2,000 and 24,000 pentosanase units per 100 pounds of flour, working the resulting mixture to form a developed dough and baking or frying the dough. The pentosanase activity (P.U.) is determined by the method of Simpson (Can. J. Microbiology, 131-139, 1954) using purified wheat pentosan as the substrate reacting at pH 5.0 at 30° C. for 30 minutes. The process may be used to prepare cakes and doughnuts as well as in the preparation of bread.

According to the patent, the incorporation of the pentosan-degrading enzyme preparation results in a surprisingly lasting softening effect on baked bread. It can be used for preparing bread in a batch procedure or in a continuous procedure. In the continuous process, the ingredients are first mixed in a mixing zone, and the mixed products are then moved to a developing zone where the dough is subjected in a continuous manner to mechanical working so as to develop the gluten. After passing through the developing zone in a continuous manner, the dough is forced through an orifice into a series of baking pans which are moved into a proofer, where the dough is allowed to rise.

"Grain Processing Opportunities with Genencor's GC123," a manufacture's literature article by Genencor, Inc., 180 Kimball Way, South San Francisco, Calif. 94080 reports that a cellulase from the microorganism *T. reesei*, namely Genencor's enzyme preparation GC123, possesses powerful pentosan degrading activity. It is further reported that the enzyme preparation contains very high levels of cellulase and beta-glucanase activities. It is taught that GC123 improved certain filtrations and reduced viscosity and is also capable of degrading wheat and barley pentosans.

Suggested applications for the Genencor enzyme preparation which are mentioned in the Genencor literature include: 1 the elimination of "sticky beak syndrome" associated with barley feeding to poultry, 2) reduction of mash viscosity, improving the watering of spent grains, and reduction in the energy requirement for spent grain drying in the distilling industry, 3) facilitation of dough formulation with less water, reduction of "stickiness", and improved performance using Anza wheat in the production of noodles and pasta products, 4) elimination of the "gummy" texture of oat products, 5) allowance of the use of wheat, oats, and rye without the usual viscosity problems in the production of cereal products and snack foods, 6) reduction in the water content when formulating grains for flaking, puffing or extrusion, 7) retarding staling of bread, 8) relaxing dough for cracker production, and facilitation of the use of "sticky" cereals in new product formulations, 9) providing new opportunities for formulating pre-mixed products, cakes and biscuits, 10) increasing the yield of prime starch in wheat wet milling, 11) facilitation of bran removal when added to tempering water, 12) upgrading millers by-products such as shorts and fiber, and 13) reducing both steeping time and starch in fiber in corn wet milling.

However, none of the above references teach or suggest the enzymatic treatment of a farinaceous material with pentosanase or beta-glucans to produce a hydrolysis product which reduces the water regain or increases the tolerance to moisture of low moisture content comestibles such as cookies, crackers, cereals, flours, flour fractions, and plant protein extracts.

SUMMARY OF THE INVENTION

The present invention provides a process for the production of low moisture content comestible products with reduced water regain properties or increased water tolerance. Reduction of water regain in comestibles results in increased shelf stability by reducing the change in moisture content over extended periods of time. By reducing diffusion of water from the surface to the interior of baked goods, for example, it is believed that the rate or propensity towards chemical reactions which may adversely affect color, odor, and taste in the comestible are reduced.

In the present invention, a farinaceous material is subjected to enzymatic treatment with an enzyme composition to substantially reduce its water-soluble hemicellulose content, said water-soluble hemicellulose comprising water-soluble pentosans and/or water-soluble beta-glucans. The hydrolysis is conducted so that a substantial portion of the hydrolysis products of the water-soluble hemicelluloses have a linear or backbone degree of polymerization of less than about 100, more suitably less than about 75, preferably less than about 50, most preferably less than or equal to about 17. It is also preferred that the linear degree of polymerization be at least 3. Thus, the most preferred range for the linear degree of polymerization is from 3 to 17. The farinaceous material is then typically subjected to a forming step followed by heating of the formed farinaceous material to reduce its water content and to inactivate the enzyme composition.

The comestible products of the present invention include baked goods such as cookies, crackers, biscuits, and snacks, hot cereals, ready-to-eat cereals, pet foods such as hard canine biscuits, dual-textured canine snacks, and dough based snacks which are filled with a non-dough filling. The comestibles of the present invention also include comminuted products such as flour, flour fractions, and cocoa. Plant protein extracts such as wheat proteins, corn proteins, and soy isolates are also produced in accordance with the present invention.

The low moisture content comestibles of the present invention typically have a moisture content of less than or equal to about 20 percent by weight, with the amount depending on the specific type of product. For baked goods, the moisture content is typically less than about 8 percent by weight, with the actual amount depending upon the type of baked good. Reducing the moisture content of hard or crisp cookies, for example to most preferably less than about 3 percent and keeping it at that low level over an extended period of time decreases fading of the cookie due to oxidative or reductive reactions over an extended period of time.

The enzyme compositions of the present invention preferably comprise endo-pentosanase, endo-beta-glucanase, or mixtures thereof. The enzyme compositions are most preferably substantially completely free of proteolytic enzymes and amylolytic enzymes. They may be also used to treat hemicellulose extracts to obtain hydrolyzates which may be incorporated into comestibles to control moisture migration.

DETAILED DESCRIPTION OF THE INVENTION

Shelf stability of low moisture content comestible products is enhanced by reducing the "moisture or water regain" of the comestibles. As used herein, "moisture regain" or "water regain" is the increase in moisture content of a product due to penetration of surface water into and through the product. It is also the ability of water to penetrate from the surface of the product throughout the product. The lower the water regain of a product, the less is the ability of water on its surface to penetrate or diffuse through the product's interior at a given temperature and given relative humidity.

Generally, the more hygroscopic and more absorptive and more hydrophilic a product is, the higher will be its water regain characteristics. Also, the more open voids and the lower the barriers to water diffusion or migration, the greater the moisture regain properties of the product. Generally, as interstices increase in size, the moisture regain properties of the product will increase. Non-edible products which would have a high water regain are a sponge, an absorbent paper towel, and a cloth diaper.

However, in foods, water regain can lead to undesirable texture, color, flavor, and aroma changes in the product resulting in shortened shelf lives. The penetration of water from the surface of comestibles to its interior can result in sogginess in products intended to be crisp, hard, or abrasive. It may also promote oxidation or other chemical reactions involving various constituents or components of the comestible product. Generally, the more mobile the system due to water migration, the more likely it is that the components of the product will interact. While comestible products may be baked, heated, or dried to reduce their moisture contents, as water contents become lower, it becomes increasingly more difficult to remove the water and to maintain the lowered moisture content over extended periods of time. The presence of highly hygroscopic or absorptive components in a product increase the difficulty in removing water and in maintaining lower water contents in the product.

In farinaceous materials, substantial amounts of water are taken up by protein and by pentosans. Some calculations for water distribution based on water uptake by isolated flour fractions, suggest 31.2 percent of the total dough water is associated with protein and 23.4 percent with pentosans. See Bushuk, W., "Distribution of Water in Dough and Bread," *Baker's Digest* Volume 40, page 38 (1966). Furthermore, on a gram per gram basis, wheat pentosans, for example, take up about 6.5 times more water than wheat proteins take up. The pentosans form a swellable network which permits relatively easy diffusion of water into and through the network. As water enters the network, it swells and retains substantial amounts of water.

Beta-glucans, like pentosans, retain large amounts of water in a swellable network. While proteins such as gluten, are generally desirably retained for machinability of doughs, cereal grains, or cereal grain fractions, the water soluble hemicelluloses often hinder machinability and increase baking or processing times because of their gummy, water-retaining nature upon hydration.

In the present invention, the absorption, hygroscopicity, and water-holding capacity of the water-soluble hemicelluloses is substantially destroyed by reducing the linear or backbone degree of polymerization of these polymers to less than about 100, more suitably less than about 75, preferably to less than about 50, most preferably to less than 17. Hydrolyzing the water-soluble hemicelluloses reduces their network-forming ability. It is believed that at a linear degree of polymerization of less than or equal to 17, the water-soluble hemicelluloses essential completely lose their ability to form a network.

The linear degree of polymerization or the backbone degree of polymerization is the number of repeating units (for example, xylose units) which are linearly connected through each molecule. For the water-soluble pentosans, for example, the arabinose side chains are not included in the linear or backbone degree of polymerization.

The water-soluble hemicelluloses include water-soluble pentosans and water-soluble beta-glucans, and mixtures thereof. "Water-soluble" is taken to mean extractable with water at a temperature of about 25° C. to about 35° C. in accordance with standard procedures for extracting pentosans or beta-glucans. See, for example, Metcalf et al, "Comparison of Chemical Composition and Properties Between Hard Red Spring and Durum Wheat Endosperm Pentosans," *Cereal Chemistry* Volume 45, pp. 539-549 (Nov. 1968) and Metcalf et al, "Structural Characterization of a Pentosan From the Water-Insoluble Portion of Durum Wheat Endosperm," *Cereal Chemistry*, Volume 45, pp. 550-556 (Nov. 1968), which are herein incorporated by reference in their entireties.

In the present invention, a substantially greater degree of hydrolysis or more specific type of hydrolysis of the water-soluble hemicelloses is used than may be typically required for substantial reductions in dough viscosities. It is believed that depending upon where in each molecule a "cut" is made, only one or two cuts in each water-soluble pentosan molecule may be needed to obtain substantial, for example from about 25% up to about 85%, reductions in dough viscosity. It is believed that depending upon the molecular weight distribution, a reduction in the number average molecular weight to about ½ or ⅓ of the initial number average molecular weight may lead to substantial reductions in dough viscosity. For example, cutting off one xylose unit in each water-soluble pentosan molecule would not have the same viscosity reducing effect as would cutting each molecule in half.

Water soluble wheat pentosans typically have a number average molecular weight of from about 50,000 to about 110,000. See, for example, Metcalf et al, "Comparison of Chemical Composition and Properties Between Hard Red Spring and Durum Wheat Endosperm Pentosans," *Cereal Chemistry* Volume 45, pp. 539-549, at pages 545-548 (Nov. 1968) where molecular weights and arabinose:xylose ratios of water soluble and water insoluble pentosans of various wheats are reported. The unhydrolyzed water-soluble wheat pentosans prior to treatment will have an average linear degree of polymerization of from about 250 to about 550 assuming that: 1) the molecular weight of a xylose unit and an arabinose unit is 132, and 2) the ratio of linear xylose units to side-chain arabinose units is 2:1. The calculations for the water-soluble wheat pentosan with a xylose:arabinose ratio of about 2:1 are:

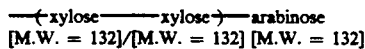
[M.W. = 132]/[M.W. = 132] [M.W. = 132]

The above "repeating unit" has a linear or backbone degree of polymerization of 2 which corresponds to a molecular weight of about 3×132=396. So, for an average linear degree of polymerization of 1, the molecular weight is 396/2=198. So, for soluble wheat pentosans having a number average molecular weight of from 50,000 to 110,000, the average linear or backbone degree of polymerization is approximately 250 (50,000/198=253) to 550 (110,000/198=555).

Thus, two "cuts" in each of the water-soluble wheat pentosan molecules would bring down the number average molecular weight to about 16,667 (50,000/3) to about 36,667 (110,000/3) with a substantial reduction in dough viscosity depending upon the molecular-weight distribution. Thus, using a molecular weight of 198 for an average linear degree of polymerization of 1, the average linear or backbone degree of polymerization for these water-soluble wheat pentosan hydrolyzates having a number average molecular weight of from 16,667 to 36,667 would be approximately from about 85 (16,667/198) to about 185 (36,667/198).

To make the low moisture content comestible products having a reduced or low water regain in accordance with the present invention, a farinaceous material is treated with an enzyme composition to produce a hydrolysis product and the enzyme composition is inactivated so that a substantial portion of the hydrolysis product has a linear degree of polymerization of less than about 100, more suitably less than about 75, preferably less than about 50, most preferably less than about 17. The enzymatic treatment substantially reduces the water-soluble hemicellulose content of the farinaceous material.

At a linear degree of polymerization of less than three, the hygroscopicity of these molecules increases compared to the hydrolyzate products having a linear degree of polymerization of three or more. Accordingly, it is preferable to control the hydrolysis so that the amount of mono- and di-saccharides which are produced are minimized. However, even if mono- and di-saccharides are produced to a substantial extent, the water regain properties of the comestible would still be significantly less than would be obtained at a linear degree of polymerization of greater than 100.

In addition, hydrolysis products having a linear degree of polymerization of three to 17 do not form networks, are low in hygroscopicity, and present a greater barrier to diffusion of water than do the mono- and di-saccharides. Accordingly, the presence of hydrolyzate products having a linear degree of polymerization of from three to 17 is particularly preferred in the present invention for reducing water regain.

In the present invention, the enzymatic treatment should be such so as to reduce the water soluble hemicellulose content of the farinaceous materials by at least 30 percent by weight, preferably at least about 50% by weight, most preferably by at least about 90 percent by weight in the production of the hydrolysis product. A linear degree of polymerization of less than about 100 should be exhibited by at least 30 percent by weight, preferably at least 50 percent by weight, most preferably by at least about 90 percent by weight of the hydrolysis product. It is preferred that substantially all of the water-soluble hemicelluloses content of the farinaceous material is hydrolyzed to a linear degree of polymerization of less than about 100 and greater than three. More preferably, substantially all of the water-soluble hemicellulose content of the farinaceous material is hydrolyzed to a linear degree of polymerization of less than or equal to 17 and greater than or equal to 3.

The low moisture content comestible products which can be made in accordance with the present invention include farinaceous products such as: a) cookies, b) yeast or chemically leavened crackers, such as graham crackers, c) biscuits, d) pet snacks such as hard canine biscuits, dual-textured pet snacks, and filled treats, e) flours for cracker and cookie production, for example, f) hot cereals, g) ready-to-eat cereals, h) cocoa powders, i) puffed or expanded snacks, and the like.

The cookies may be single dough crisp or soft cookies, multitextured two dough cookies baked from a composite dough piece having an inner or filler dough bakeable to a soft or chewy texture which is enrobed by an outer or casing dough bakeable to a firmer and tender texture, cookies which are filled with a non-dough filling such as a cream or pudding, sandwich cookies, and the like. The single or multiple dough cookies may be chocolate chip cookies, oatmeal cookies, sugar cookies, vanilla cookies, fudge cookies, and the like. In multiple dough cookies the enzyme treated dough may be both doughs or either dough, preferably the outer dough. The multitextured cookies and filled cookies may be produced by coextrusion to form an extrudate rope which may be severed to form enrobed dough pieces in known manner.

Comestible products which are derived from farinaceous materials may also be produced in accordance with the present invention. These comestibles include plant protein extracts such as wheat gluten, corn protein, and soy isolates.

Typically, the comestible products of the present invention will have at least about 0.035 percent by weight of the hydrolysis product having a linear degree of polymerization of less than about 100, based upon the weight of the starch in the product, on a solids basis.

As used herein, the term "farinaceous" includes any material containing starch, made from starch, rich in or consisting of starch.

The farinaceous materials which may be subjected to the enzymatic treatment in accordance with the present invention include bleached or unbleached flour, flour fractions, and mixtures thereof, starch, such as corn starch, wheat starch, rice starch, potato starch, tapioca starch, and mixtures thereof, whole cereal or cut cereal grains such as wheat, corn, oats, barley, rice, and mixtures thereof, cereal grain fractions such as bran, germ, and endosperm fractions, and plant protein extracts such as commercially available wheat and corn gluten, and commercially available soy isolates.

Typically, the farinaceous materials which are treated in the present invention will contain at least about 0.3 percent by weight of water-soluble hemicelluloses (water-soluble pentosans, or water-soluble beta-glucans, and mixtures thereof) based upon the dry weight of the farinaceous material.

The flours which may be used in the present invention include wheat, corn, rice, barley, rye, oat, potato, tapioca, graham, and mixtures thereof. The preferred flours for making the baked comestibles of the present invention are wheat flours. Typical wheat flours which may be used are hard red winter, hard red spring, soft red winter, soft white east, soft white west, soft white club, and durum wheat flour, and mixtures thereof. Particularly suited for the crackers of the present invention are the hard red wheat flours.

Typical pentosan contents (total pentosan and water-soluble pentosan) for various flour types are presented in Table 1 wherein all percentages are on a dry basis:

TABLE 1

| TYPICAL PENTOSAN CONTENTS BY FLOUR TYPE | | |
|---|---|---|
| Flour Type | % Total | % Soluble |
| Hard red winter | 1.55 | 0.44 |
| Hard red spring | 1.50 | 0.42 |
| Soft red Winter | 1.49 | 0.38 |
| Soft white east | 1.47 | 0.39 |
| Soft white west | 1.58 | 0.47 |
| Soft white club | 1.41 | 0.45 |
| Durum | 1.45 | 0.36 |

A typical dry basis composition of hard red spring wheat is presented in Table 2:

TABLE 2

| | TYPICAL DRY BASIS COMPOSITION OF HARD RED SPRING WHEAT | | | |
|---|---|---|---|---|
| | Weight % | Weight % of Dry Product | | |
| Product | Of Total Kernel | Protein % | Starch % | Pentosans % |
| Kernel | 100.0 | 17.7 | 61.3 | 6.0 |
| Patent Flour | 65.3 | 16.4 | 77.1 | 1.9 |
| 1st Clear Flour | 5.2 | 17.6 | 73.0 | 2.3 |
| 2nd Clear Flour | 3.2 | 20.9 | 65.1 | 3.0 |
| Bran | 16.4 | 19.3 | 13.5 | 20.9 |

An approximate chemical composition of a typical commercial mill mix of hard red spring wheat and its principal mill products is presented in Table 3:

TABLE 3

| COMMERCIAL MIX OF HARD RED SPRING WHEAT Proximate chemical composition of a commercial mill mix of hard red spring wheat and its principal mill products[a]; chemical composition (13.5% m.b.) | | | | | | | | |
|---|---|---|---|---|---|---|---|---|
| Product | Proportion of Wheat % | Protein[b] % | Fat % | Ash % | Starch % | Pentosans % | Sugars[c] % | Undetermined % |
| Wheat | 100.00 | 15.3 | 1.9 | 1.85 | 53.0 | 5.2 | 2.6 | 6.8 |
| Patent Flour | 65.3 | 14.2 | 0.9 | 0.42 | 66.7 | 1.6 | 1.2 | 1.4 |
| 1st-Clear Flour | 5.2 | 15.2 | 1.4 | 0.65 | 63.1 | 2.0 | 1.4 | 2.8 |
| Milkbone Flour | 3.2 | 18.1 | 2.4 | 1.41 | 56.3 | 2.6 | 2.1 | 3.6 |
| 2nd Clear Flour | | | | | | | | |
| Red Dog Flour | 1.3 | 18.5 | 3.8 | 2.71 | 41.4 | 4.5 | 4.6 | 11.0 |
| Shorts | 8.4 | 18.5 | 5.2 | 5.00 | 19.3 | 13.8 | 6.7 | 18.0 |
| Bran | 16.4 | 16.7 | 4.6 | 6.50 | 11.7 | 18.1 | 5.5 | 23.5 |
| Germ | 0.2 | 30.9 | 12.6 | 4.30 | 10.0 | 3.7 | 16.6 | 8.4 |

[a]Compiled from USDA mimiographed publication ACE-189.
[b]Nitrogen × 5.7.
[c]Expressed as glucose.

An approximate carbohydrate composition of typical commercial wheat fractions is presented in Table 4:

TABLE 4

| APPROXIMATE CARBOHYDRATE COMPOSITION OF TYPICAL COMMERCIAL WHEAT FRACTIONS | | | |
|---|---|---|---|
| | Percent of Components in Total Carbohydrate | | |
| Nature of Carbohydrate | Endosperm % | Germ % | Bran % |
| Hemicelluloses | 2.4 | 15.3 | 43.1 |
| Cellulose | 0.3 | 16.8 | 35.2 |
| Starch | 95.8 | 31.5 | 14.1 |
| Sugars | 1.5 | 36.4 | 7.6 |

TABLE 4-continued
APPROXIMATE CARBOHYDRATE COMPOSITION
OF TYPICAL COMMERCIAL WHEAT FRACTIONS

| Nature of Carbohydrate | Percent of Components in Total Carbohydrate | | |
|---|---|---|---|
| | Endosperm % | Germ % | Bran % |
| Total Carbohydrates | 86.0 | 50.5 | 70.0 |

Typically, the farinaceous materials utilized in the present invention have a water-soluble hemicellulose (water-soluble pentosan, water-soluble beta-glucan, and mixtures thereof) content of at least about 0.3 percent by weight and a total hemicellulose content of at least about 1.4 percent by weight, on a dry basis.

The enzyme compositions for treating the farinaceous material in accordance with the present invention comprise a pentosanase, a beta-glucanase, or mixtures thereof. Most preferably, the enzyme compositions are protease free so as to avoid destruction of the functionality of the proteins in the farinaceous materials. Also, they are preferably substantially free of amylases so as to avoid destruction of the functionality of the starch. Most preferably the pentosanase will be substantially all endo-pentosanase and the beta-glucanase will be substantially all endo-beta-glucanase so as to minimize the production of monosaccharides and/or di-saccharides. The enzyme composition may include exo-pentosanase, exo-beta-glucanase, cellulases, xylanases, and other carbohydrate enzymes although the use of substantially all endo-pentosanase and endo-beta-glucanase is preferred. The enzyme preparations which may be used can be commercially available preparations or commercial preparations which have been further purified or fractionated.

The enzymes may be used at temperatures and pH conditions normally recommended by their manufacturers or at conditions which are optimal for pentosanase activities.

A commercially available enzyme preparation which may be used in the present invention is GC123, manufactured by Genencor, Inc., 180 Kimball Way, South San Francisco, Calif. 94080. It is described in their literature as a cellulase from the microorganism *Trichoderma reesei* which possesses powerful pentosan degrading activity. It is believed to comprise endo-cellulase, beta-glucanase, pentosanase, and beta-glucosidase. According to the Genencor literature, when evaluating GC123 in cereal grain applications the enzyme should be added at about 0.2 percent w/w based on grain. It is indicated that in many applications this dosage can be substantially reduced. It is further indicated that optimal operating pH for the important activities in GC123 are generally centered around pH 4.8. It is indicated that considerable flexibility does exist. Typically, it is reported, pH adjustment is not required when treating cereal grains suspended in tap water (pH approximately 6.2). According to the literature, optimal activity is generally found at about 50° to 60° C. (122° to 140° F.). The enzymes, it is stated, are active at lower temperatures, but work less quickly. Higher temperatures (to approximately 70° C.) may be used for short incubation times but the activity is soon lost due to thermal inactivation.

In producing the comestible products of the present invention, such as baked goods, the enzyme composition should generally be added with the water used in preparing the comestible. This assures a more homogeneous distribution of the enzyme through the farinaceous material, such as flour, upon which it is intended to act. In the production of cookies or crackers, the enzyme composition may be added with a minor portion of the water or in undiluted form after the flour is dumped into the mixer. This procedure may be used to avoid higher temperatures which may reduce enzyme activity or viability encountered for the addition or incorporation of other dough ingredients. For example, in the production of crackers, a fat or shortening is typically heated or melted for incorporation into the dough at the creaming stage. The enzyme may be added after the flour is dumped into the creamed mixture. A dough is then formed by mixing flour and the enzyme into the remaining ingredients. A rotary cookie dough may be produced, for example, by dry-blending cocoa powder and sugar to form a substantially homogeneous blend, creaming in water and lard to form a creamed mixture, dumping flour onto the creamed mixture, adding a dose of the enzyme on top of the flour, and then mixing the ingredients to form a dough.

The amount of enzyme which is used in the processes of the present invention will depend upon its endo-pentosanase and/or endo-beta-glucanase enzymatic activity. The enzymatic activity should be sufficient so as to provide a hydrolysis product in which a substantial portion has a linear degree of polymerization of less than about 100 within normal or conventional processing times (e.g. conventional mixing and lay times) for making the product (e.g. cookies, crackers, or snacks). Enzymatic activity, for purposes of the present invention is defined as the number of reducing sugar ends produced per mole of unhydrolyzed or native hemicellulose. Endo-pentosanase enzymatic activity is the number of reducing sugar ends produced per mole of unhydrolyzed pentosans (water soluble and water insoluble). Endo-beta-glucanase activity is the number of reducing sugar ends produced per mole of beta-glucans. The number of reducing sugar ends can be determined by standard analytical techniques known to those skilled in the art such as the Nelson-Somogyi technique for reducing sugars and the phenol-sulfuric acid method for total sugars. See also, Simpson, F. J., "Microbial Pentosanases. I. A Survey of Microorganisms For The Production of Enzymes That Attack The Pentosans of Wheat Flour," *Canadian J. of Microbiology*, vol. 1, no. 2, pp 131–139 (Oct. 1954), which is herein incorporated by reference in its entirety, where a unit of pentosanase was defined as the amount of enzyme that will reduce by 50% the viscosity of a standard substrate in 30 minutes at 30° C.

The hydrolysis products may also be defined in terms of a dextrose equivalent (DE) in the case of beta-glucans and in terms of a xylose equivalent (XE) in the case of pentosans. A dextrose equivalent (DE) is well known and is defined as the concentration of reducing sugars present expressed as dextrose and calculated as a percentage of the dry substance. A xylose equivalent or XE is defined as the concentration of reducing sugars present expressed as xylose and calculated as a percentage of the dry substance. Unhydrolyzed or native pentosan would have an XE equal to zero and xylose would have an XE equal to 100. The xylose equivalent (XE) may be calculated as:

$$XE = 100/(\bar{M}n/150)$$

Where $\overline{M}_n$ is the number average molecular weight of the pentosan hydrolyzate,
and 150 is the molecular weight of xylose.

The XE may be correlated with the linear degree of polymerization. For example, for a hard red winter wheat having a pentosan content of about 1.55 percent, a water-soluble pentosan content of about 0.44% by weight with a number average molecular weight of about 50,000, and a xylose:arabinose ratio of about 2:1, hydrolysis to a:

| Linear degree of polymerization of | would result in an approximate XE of |
|---|---|
| 3 | 36.0 |
| 17 | 7.0 |
| 50 | 2.3 |
| 100 | 1.1 |

The enzymes are inactivated in the present invention preferably by the application of heat. In the preparation of baked goods, the inactivation is preferably performed during the baking step, or may be achieved by microwave heating.

The low moisture content farinaceous products of the present invention should have a moisture content of less than or equal to about 20 percent by weight. For farinaceous materials which are in comminuted form such as flours, flour fractions, and cocoa, the moisture content of the final product is typically greater than the moisture content of other finished goods such as baked goods. For flours and flour fractions the moisture content is typically from about 11 percent to about 16 percent by weight. Cocoa will typically have a moisture content of from about 6 percent to about 15 percent by weight. Finished baked goods will typically have a moisture content of less than or equal to about 8 percent by weight, preferably less than about 5 percent by weight. For the production of hard or crisp cookies, crackers, and sandwich cookies containing a filler cream, the water content is preferably less than about 3 percent by weight, exclusive of inclusions such as nuts, and chocolate chips. For soft variety cookies, and dual-textured cookies the water content is preferably less than about 8 percent by weight, preferably less than about 5 percent by weight.

The plant protein extracts, such as gluten, of the present invention will typically have a moisture content of up to about 7 percent by weight.

Hot cereals, typically in flake form for reconstitution by the consumer, will typically have a moisture content of less than about 8 percent by weight. Ready-to-eat cereals in accordance with the present invention will generally have a moisture content of less than about 8 percent by weight, preferably less than 5 percent by weight, more preferably less than about 3 percent by weight.

For each of the above water contents, the product is processed e.g., by baking, so as to obtain a moisture content which remains essentially the same for extended periods of time, preferably for at least six months, more preferably for at least about one year.

Also, the above moisture contents, in the case of baked goods, refer to the dough-based portion of the good and do not include a non-dough filler, for example.

In addition to the advantage of low or reduced moisture regain properties, the use of the enzyme compositions and the treatment of farinaceous material in accordance with the present invention provides additional advantages.

In the production of flours and flour fractions, improved uniformity can be obtained by reduction in their pentosan contents. Additionally, the hydrolyzate products are substantially non-digestible thereby permitting the production of low calorie flour ingredients which do not swell by controlled hydrolysis of the pentosans to produce particular ranges of an oligoxylan component with desired molecular weight distribution.

Increased functionality of extracted plant proteins such as wheat gluten, corn protein, and soy isolates can be obtained in the present invention. For example, the performance of gluten as an ingredient or a flour component can be improved by removal of pentosans to enhance film formation and improve product quality in the production of puffed, expanded, or laminated baked goods. Baked goods may, accordingly, be produced with possible reductions in the amount of leavening agent. Also, the performance of gluten may be improved by removal of pentosans to increase the extent of thermoset and post-cure by microwave heating.

Use of the enzyme compositions in accordance with the present invention may also result in softer pumpable doughs. This may be of particular advantage for the continuous production of crackers and cookies and baked pet snacks, such as biscuits, dual-textured pet snacks and filled pet treats. Additionally, machinable doughs, particularly for crackers, dual-textured pet snacks produced from coextruded doughs, and canine biscuits may be produced efficiently without addition of bisulfite. It is also believed that doughs with greater uniformity are obtained because of hydrolysis of cell wall components by cell-wall hydrolases present in the enzyme compositions.

The moisture content of the doughs should be such so as to provide for proper handling and machining, such as forming, shaping, sheeting, and lamination of the doughs. Lower moisture content doughs may be used in view of the dough-viscosity lowering effect of the enzyme compositions, depending on the type and amount of farinaceous materials and the comestible. The use of lower moisture content doughs can result in a reduced energy baking process.

In the production of graham crackers, dough moisture content reductions of 20-25% by weight or more may be needed to obtain a machinable enzyme-treated graham cracker dough. Typically, a conventional graham cracker dough may have an added water content of about 21% by weight, based upon the total weight of the flours. Treatment of the graham cracker dough with a pentosanase composition may require reduction of the added water content to less than or equal to about 17% by weight, based upon the total weight of the flours, to reduce dough softness and to obtain a more cohesive, machinable dough.

However, generally the use of conventional, higher dough moisture contents is preferred, with the moisture being generally released more rapidly or to a greater extent in the higher moisture content enzyme treated doughs in a given baking time and at a given baking temperature. In the production of cookies which contain relatively low water contents, such as rotary molded sandwich cookies containing high amounts of cocoa, reducing the water content of the enzyme treated dough may result in a non-cohesive, crumbly dough. The added water content of these enzyme treated doughs should typically be kept at levels of about 25% by weight or more, based upon the weight of the flour.

Additionally, surface drying may be retarded during holding time of doughs and during machining time of sheeted doughs, and laminated doughs through the enzymatic treatment utilized in the present invention. This may result in a reduction of "checking" or surface cracking in crackers, for example. It is believed that even though water evaporates from the dough surface, it is replenished by water from the interior which is no longer held by the highly absorbent pentosans. The laminated doughs may be formed by laminating separate dough sheets or by laminating a dough sheet upon itself to form two, three, or more layers.

In the production of crackers of the fermented type, involving a sponge stage and a dough-up stage, the enzyme composition may be added in the sponge stage to increase the softness of the sponge and simulated accelerated fermentation. The enzyme composition may also be added in the dough-up stage.

The present invention also encompasses the retardation of the fading of baked products during storage. The products, such as cookies, may be baked to a lower moisture content than usual to retard fading without a decrease in eating quality. Improvement of eating quality of cookies made with hard flours treated with the enzyme compositions in accordance with the methods of the present invention may be increased by the use of soluble sucrose, high fructose corn syrup and high dextrose equivalent corn syrups.

In the production of pet snacks, such as hard canine biscuits, coextruded two-dough dog treats, and dough-based filled products, increased abrasiveness and teeth cleaning may be achieved by baking to lower moisture contents. Also, improved moldability of the doughs with reduced fissures in and reduced breakage of the final product may be achieved with the enzymatic treatment utilized in the present invention.

Proteolytic enzymes, such as fungal proteases may be used to hydrolyze a portion of the proteins in high protein content doughs, such as a canine biscuit dough, so as to soften the dough and improve its moldability. However, it has been found that the use of proteases in canine biscuit production tends to result in excessive discoloration or scorching of the biscuit. It is believed that the scorching is due to Maillard-type reactions resulting from the protein hydrolysis products. The use of amylolytic enzymes to soften the biscuit dough tends to result in excessive stickiness of the dough to the dough forming equipment. It may also result in reduced softness of the biscuit. The use of a pentosanase composition which is substantially free of protease and amylase avoids these problems.

In cereal production, the viscosity and adhesiveness of cooked oats may be decreased to facilitate the production of shredded oats by the use of the enzyme compositions in accordance with the present invention. To produce shredded oats, whole oat groats may be cooked with water at about 80° to 95° C., cooled to about 65° to 75° C., followed by enzyme addition and steeping. The steeping water is then drained, the enzymatically treated oats are then surface dried by airflow, followed by tempering and then shredding. The shredding may be performed using counter-rotating shredding rolls, at least one of which is grooved, to produce net-like sheets. The net-like sheets may be laminated into three or more layers and the laminate is then cut or scored into pieces which are baked into shredded oat biscuits. In a modification of the process, the enzyme may be sprayed onto the surface dried oats, the sprayed oats may then be tumble-dried, followed by tempering and then shredding.

Shredded oats may also be produced by spraying a mixture of water and the enzyme composition onto oat flour with mixing to form free-flowing agglomerates. The agglomerates may then be subjected to microwave energy, then tempered, followed by shredding.

Additionally, the viscosity and adhesiveness of the cooked oats can be decreased to improve the mouthfeel of hot oat-based cereals. Oat groats, cut oat groats, or rolled oats may be cooked, cooled, then treated with the enzyme composition, followed by drying, tempering, flaking between flaking rolls and then drying or toasting. The enzyme may be added during steeping of the cooled oats or may be sprayed onto the oats prior to flaking. The oat flakes may be mixed with hot water to obtain hot cereals which retain a low viscosity for extended periods of time. The oat flakes may also be used as an ingredient in the production of crisp oatmeal cookies.

Cereal products may also be produced by mixing cooked oat flakes, such as commercially available hot cereal oat flakes or rolled oats with hot water, cooling the mixture to less than about 75° C., preferably to about room temperature to about 35° C., followed by the addition of the enzyme composition with optional additional water to form a slurry. The slurry may be used as an ingredient in the production of oatmeal cookies or hot cereals and ready-to-eat cereals. The slurry may be sprayed onto products or mixed in with the other ingredients before inactivation of the enzyme.

Hemicellulose hydrolyzates having linear degrees of polymerization in accordance with the present invention may be produced by enzymatic treatment of extracted hemicelluloses, such as water-soluble pentosans or beta-glucans. The hydrolyzates may be incorporated into comestibles to control moisture migration or water regain.

The present invention is further illustrated in the following examples. Unless otherwise stated, enzyme dosages or concentrations are per gram of dry substance. Also, all temperatures are in degrees F and percentages, ratios, and proportions are by weight unless indicated to the contrary:

EXAMPLE I

A flour having reduced water regain may be prepared by treating an unbleached hard red winter wheat flour having a total pentosan content of about 1.55 percent, and a water-soluble pentosan (number average molecular weight of 50 kilodaltons) content of about 0.44% with an enzyme composition having an endo-pentosanase activity of about 5.0 reducing sugar ends per mole of pentosan, and essentially no proteolytic and no amylolytic activity.

To 100 grams of the flour there may be added with mixing, the enzyme composition in an amount, at a temperature and concentration, and for a time which are sufficient to produce oligoxylans having an XE value of greater than about 1.1. The enzyme composition is first mixed with water. The flour, water, and enzyme composition may be mixed to obtain a substantially uniform dough. The enzymes may be inactivated and the dough may be dried to a moisture content of about 16% by weight to obtain a product wherein at least 90% by weight of the water soluble pentosans are hydrolyzed to a linear degree of polymerization of less than about 100. The dried product may then be comminuted to obtain a powder.

EXAMPLE II

A cracker having reduced water regain may be prepared as in Example I except 2 grams of a leavening agent may be included in the dough, the dough may be rolled into a sheet and cut into circular pieces, and the pieces may be baked: a) to inactivate the enzymes to obtain a moisture content of about 4% by weight and b) to obtain a product wherein at least 90% by weight of the water soluble pentosans are hydrolyzed to a linear degree of polymerization of less than about 100.

EXAMPLE III

A crisp cookie having reduced water regain and increased fading resistance may be prepared using the same unbleached flour and enzyme composition used in making the flour of Example I. The ingredients and their relative amounts which may be used are:

| Ingredient | Parts By Weight |
| --- | --- |
| Unbleached wheat flour of Example I (about 12% by weight water) | 100.0 |
| Sucrose, granulated | 82.0 |
| Vegetable shortening | 60.0 |
| Sodium bicarbonate | 2.6 |
| Salt | 1.6 |
| Flavoring | 0.5 |
| Chocolate drops | 60.0 |
| Water (room temperature) | 23.5 |
| Enzyme Composition of Example I | |

The enzyme composition of Example I may be used in an amount and during a period of time which are sufficient to produce oligoxylans having an XE value of greater than about 1.1. The dough may be prepared at room temperature using a mixer running at low speed. One-half of the sucrose, together with the shortening, salt, and flavoring are placed in the mixing bowl and mixed for about 3 minutes to obtain a smooth consistency. The enzyme can be premixed with the room temperature water and the pre-mix may then be added to the mixing bowl. The mixing can be continued for about 1 minute. The flour and sodium bicarbonate may be added and the mixing continued for about a further 2 minutes. The remaining sucrose may then be added and the mixing continued for about a further 2 minutes. Finally, the chocolate chips can be added and the mixing continued for about a further 1 minute to prepare the finished casing dough. The dough may be permitted to lay at room temperature, then formed into pieces, and the pieces may then be baked to: a) inactivate the enzymes and to obtain cookies having a moisture content of about 3% by weight, based upon the weight of the cookies, exclusive of the chocolate chips, and b) to obtain a product wherein at least 90% by weight of the water soluble pentosans are hydrolyzed to a linear degree of polymerization of less than about 100.

EXAMPLE IV

A cookie may be produced as in Example 3 except the amount of the enzyme composition may be increased and the lay time may be increased to produce oligoxylans having an XE value greater than about 7 and to obtain a product wherein at least 90% by weight of the water soluble pentosans are hydrolyzed to a linear degree of polymerization of less than about 17.

EXAMPLE V

A gluten product having reduced water regain and which is substantially free of water-soluble pentosans may be produced by treating a commercially available vital wheat gluten with the enzyme composition of Example I, in an amount, at a temperature and concentration, and for a time which are sufficient to produce oligoxylans having an XE value of greater than about 1.1. The enzyme composition may be first mixed with water and then with the vital wheat gluten to obtain a substantially uniform mass. The enzymes may be inactivated and the mass dried to a moisture content of about 16% by weight to obtain a product wherein at least 90% by weight of the water soluble pentosans are hydrolyzed to a linear degree of polymerization of less than about 100. The dried product may be comminuted to obtain a powder.

EXAMPLE VI

A hard canine biscuit having reduced water regain and increased abrasiveness may be prepared using the same unbleached flour and enzyme composition used in making the flour of Example I. The ingredients and their relative amounts which may be used are:

| Ingredient | Parts By Weight |
| --- | --- |
| Unbleached wheat flour of Example I (about 12% by weight water) | 100 |
| Soybean Meal | 14 |
| Animal Fat | 3.4 |
| Meat and Bone Meal | 11 |
| Salt | 1 |
| Natural Flavors | 1.8 |
| Wheat Meal | 4.2 |
| Water (140° F.) | 52 |
| Vitamin and Mineral Preblend | 2.7 |
| Acidulant | 0.4 |
| Enzyme Composition of Example I | |

The enzyme composition of Example I may be used in an amount and during a period of time which are sufficient to produce oligoxylans in the dough having an XE value of greater than about 1.1. The dough may be prepared at room temperature using a mixer running at low speed. The dry ingredients may be preblended in the mixer so as to obtain a substantially uniform mixture. The 140° F. water may be added to the preblend with mixing which reduces the water temperature. The enzyme composition may then be added with mixing to form a first stage dough. The melted fat, at about 150° F., may then be added with mixing to form the finished dough. The dough may then be formed into pieces by molding, and the pieces may then be baked to: a) inactivate the enzymes and to obtain biscuits having a moisture content of about 6% by weight, based upon the weight of the biscuits, and b) to obtain a product wherein at least 90% by weight of the water soluble pentosans are hydrolyzed to a linear degree of polymerization of less than about 100.

What is claimed is:

1. A method for reducing color fading in cookies which fade during storage comprising forming a machinable cookie dough by admixing cookie ingredients comprising a flour which contains water-soluble hemicelluloses, sugar, shortening or fat, and water with an enzyme composition comprising a pentosanase which hydrolyzes said water-soluble hemicelluloses to obtain hydrolysis products with reduced water holding capacity, and baking the dough to obtain cookies having a moisture content of less than about 5% by weight, exclusive of inclusions, the water soluble hemicellulose content of said flour being reduced by at least about 30% by weight in the production of said hydrolysis products, and at least about 30% by weight of said hydrolysis products having a linear degree of polymerization of 3 to less than about 100, said enzymatic treatment and said cookie moisture content being such so that the color of the cookies after baking remains essentially unchanged during shelf storage for at least about six months.

2. A method as claimed in claim 1 wherein the water soluble pentosan content of said flour is at least about 0.3% by weight, based upon the dry weight of said flour.

3. A method as claimed in claim 1 wherein the enzyme composition comprises an endopentosanase.

4. A method as claimed in claim 1 wherein the enzyme composition is substantially free of proteases and amylases.

5. A method as claimed in claim 1 wherein the enzyme composition consists essentially of a pentosanase.

6. A method as claimed in claim 1 wherein the dough is formed into pieces and the pieces are baked to inactivate the enzyme composition.

7. A method as claimed in claim 1 wherein the enzyme composition is added to the flour and the ingredients are mixed to form said cookie dough.

8. A method as claimed in claim 1 wherein the dough comprises cocoa, and the added water content of the dough is at least 25% by weight, based upon the weight of the flour.

9. A method as claimed in claim 1 wherein the enzyme-treated cookie dough is used to enrobe another cookie dough and the composite dough is baked to obtain a dual-textured cookie.

10. A method as claimed in claim 1 wherein the enzyme composition is derived from *trichoderma reesei*.

11. A method as claimed in claim 10 wherein said enzyme composition comprises endo-cellulase, beta-glucanase, pentosanase, and beta glucosidase.

12. A method as claimed in claim 10 wherein said enzyme composition consists essentially of pentosanase.

13. A method as claimed in claim 1 wherein the machinable dough is formed with a decreased amount of water.

* * * * *